United States Patent [19]

Hungerbühler et al.

[11] Patent Number: 5,110,582
[45] Date of Patent: May 5, 1992

[54] HAIR-SETTING PREPARATION

[75] Inventors: Walter Hungerbühler; Hubert Meindl, both of Riehen, Switzerland

[73] Assignee: BASF Aktiengesellschaft, Ludwigshafen, Fed. Rep. of Germany

[21] Appl. No.: 81,636

[22] Filed: Aug. 3, 1987

Related U.S. Application Data

[63] Continuation of Ser. No. 693,216, Jan. 18, 1985, abandoned, which is a continuation of Ser. No. 594,955, Apr. 2, 1984, abandoned, which is a continuation of Ser. No. 360,030, Mar. 19, 1982, abandoned.

[30] Foreign Application Priority Data

Mar. 25, 1981 [CH] Switzerland .......................... 2019/81

[51] Int. Cl.$^5$ .......................... A61K 7/06; A61K 9/12
[52] U.S. Cl. .................... 424/47; 424/DIG. 1; 424/59; 424/81; 526/307.6; 526/307.7
[58] Field of Search ........................ 424/47, 81, DIG. 1

[56] References Cited

U.S. PATENT DOCUMENTS

| | | | |
|---|---|---|---|
| 3,025,219 | 3/1962 | Maeder | 424/81 |
| 3,112,296 | 11/1963 | Maeder | 526/240 |
| 3,927,199 | 12/1975 | Micchelli et al. II | 424/81 |
| 4,192,861 | 3/1980 | Michelli et al. I | 424/47 |
| 4,240,450 | 12/1980 | Grollier et al. | 424/47 |
| 4,315,910 | 2/1982 | Nowak, Jr. et al. | 424/47 |

FOREIGN PATENT DOCUMENTS

| | | | |
|---|---|---|---|
| 698796 | 12/1964 | Canada | 424/47 |
| 506538 | 3/1975 | Japan | 424/47 |

*Primary Examiner*—Dale R. Ore
*Attorney, Agent, or Firm*—Oblon, Spivak, McClelland, Maier & Neustadt

[57] ABSTRACT

A hair-setting preparation which contains
(1) a solution of at least one terpolymer in an anhydrous or water-containing organic solvent, the terpolymer having been prepared by the copolymerization of
  (a) an N-alkylacrylamide or N-alkylmethacrylamide having 1 to 4 carbon atoms in the alkyl moiety, with
  (b) a $C_1$–$C_4$-alkyl ester or $C_1$–$C_4$-hydroxyalkyl ester of acrylic acid or methacrylic acid, and with
  (c) an $\alpha,\beta$-unsaturated moncarboxylic acid or dicarboxylic acid, and at least 50% of the carboxyl groups in the terpolymer having been neutralized by a lower organic base, and
(2) a propellent which consists of at least 30% by weight, based on the total propellent, of a halogen-free propellent gas, in particular a hydrocarbon.

5 Claims, No Drawings

HAIR-SETTING PREPARATION

This application is a continuation of application Ser. No. 06/693,216, filed on Jan. 18, 1985, now abandoned, which is a continuation of abandoned application Ser. No. 06/594,955, filed Apr. 2, 1984, which is a continuation of application Ser. No. 06/360,030 filed Mar. 19, 1982 now abandoned.

The present invention relates to a hair-setting preparation containing an acrylic-based terpolymer as the main active substance. The novel hair-setting preparation is employed in particular in hair sprays, and especially in water-free or water-containing aerosol sprays, using non-halogenated propellent gases.

Recently, halogen-containing propellent gases have been increasingly replaced by halogen-free propellent gases for ecological reasons. However, it has been established that carboxylated resins in alcoholic formulations, such as those preferably used as aerosol hair sprays, have a lower solubility in the presence of halogen-free propellent gases, for example propane, butane, isobutane or mixtures thereof, than in the case where fluorochlorohydrocarbons are used. This can lead to precipitation of thepolymers during the storage period, whereby the sprays become unusable.

Long-chain amines are proposed in German Offenlegungsschrift 2,917,504, by way of example, as neutralising agents which increase the compatibility of the polymers with the said propellent gases. In German Offenlegungsschrift 2,317,484, halogenated propellent gases containing small proportions of isobutane can be employed when using polymers which contain t-octylacrylamide as one of the components. In this case, the effect of using the long-chain t-octylacrylamide is a better compatibility with the propellent gases than when using shorter-chain acrylamides. It has now been found that terpolymers which are obtained from monomers with substituents containing at most 4 carbon atoms, and the carboxyl groups of which are neutralised by the short-chain amines or aminoalcohols conventional in cosmetics, have such a good compatibility with halogen-free propellent gases that the latter can replace 30-100% of the freon propellent gases in aerosol spray formulations.

The present invention thus relates to a hair-setting preparation which contains (1) a solution of at least one terpolymer in an anhydrous or water-containing organic solvent, the terpolymer having been prepared by the copolymerisation of
  (a) an N-alkylacrylamide or N-alkylmethacrylamide having 1 to 4 carbon atoms in the alkyl moiety, with
  (b) a $C_1$–$C_4$-hydroxyalkyl ester or, preferably, $C_1$–$C_4$-alkyl ester of acrylic acid or methacrylic acid, and with
  (c) an $\alpha,\beta$-unsaturated monocarboxylic acid or dicarboxylic acid, and at least 50% of the carboxyl groups in the terpolymer having been neutralised by a lower organic base, and (2) a propellent which consists of at least 30% by weight, based on the total propellent, of a halogen-free propellent gas.

The terpolymer used in the hair-setting preparation is advantageously derived from a mixture of monomers which contains 40 to 60% by weight of component (a), 35 to 50% by weight of component (b) and 3 to 11% by weight, preferably 4 to 9% by weight, of component (c). The percentages are based on the total weight of the mixture of monomers.

The N-substituted acrylamides or methacrylamides which can be used as monomers (a) are substituted by alkyl radicals which contain 1 to 4 carbon atoms. Examples of acrylamides and methacrylamides of this type which can be used are N-methylacrylamide, N-ethylacrylamide, N-propylacrylamide, N-n-butylacrylamide, N-isopropylacrylamide, N-sec.-butylacrylamide, N-tert.-butylacrylamide and the corresponding methacrylamides. The acrylamides, and in particular N-tert.-butylacrylamide, are preferred.

Examples of alkyl esters of acrylic acid or methacrylic acid which can be used as monomers (b) are methyl, ethyl, propyl, isopropyl or n-butyl acrylate or methacrylate, the acrylates being preferred to the methacrylates. Of the acrylates, ethyl acrylate is particularly preferred. Furthermore, acrylates or methacrylates containing hydroxyl groups, for example hydroxyethyl acrylate, hydroxypropyl acrylate or hydroxyethyl methacrylate, can also be used as component (b).

The $\alpha,\beta$-unsaturated monocarboxylic acids or dicarboxylic acids suitable as component (c) have 3 to 6 carbon atoms as a rule. Examples of suitable $\alpha,\beta$-unsaturated monocarboxylic or dicarboxylic acids are acrylic acid, methacrylic acid, crotonic acid, maleic acid, fumaric acid or itaconic acid. It is also possible to use the $C_1$- to $C_4$-alkyl half-esters of the said dicarboxylic acids. Preferred components (c) are methacrylic acid and, in particular, acrylic acid.

Particularly preferred terpolymers are obtained from 45 to 55% by weight of N-tert.-butylacrylamide, 35 to 45% by weight of ethyl acrylate and 5 to 8% by weight of acrylic acid.

The copolymerisation for the preparation of the terpolymers which can be used according to the invention is advantageously carried out in a water-miscible organic solvent, which can also be mixed with water. The organic solvent can be used by itself or as a mixture of two or more components.

Examples of water-miscible organic solvents are aliphatic $C_1$–$C_3$-alcohols such as methanol, ethanol or propanols, ketones such as acetone or diacetone-alcohol, and also N-methylpyrrolidone. The reaction is preferably carried out in a solvent mixture consisting of a $C_1$–$C_3$-alkanol and water, or of a $C_1$–$C_3$-alkanol and acetone, for example ethanol/water, isopropanol/water, ethanol/methanol/water, ethanol/isopropanol/water or ethanol/acetone.

To carry out the copolymerisation, it is advantageous first to prepare a solution of the mixture of monomers. It is also possible to use separate solutions of the corresopnding monomers.

The copolymerisation is carried out as a rule in the presence of a polymerisation initiator, which can be present in the solutions of the monomers or, preferably, is added to the reaction mixture in the form of an alkanolic solution.

The amounts in which the polymerisation initiator is added to the reaction mixture vary between 0.001 and 0.5% by weight, based on the mixture of monomers. Examples of suitable polymerisation initiators are azo-iso-butyronitrile or, in particular, organic peroxides such as dicumyl peroxide, di-tert.-butyl peroxide, diacetyl peroxide, dibenzoyl peroxide, benzoyl acetyl peroxide, dilauroyl peroxide, t-butyl perbenzoate, tert.-butyl peroxy-neodecanoate or, in particular, tert.-butyl peroctoate.

The copolymerisation is generally carried out at an elevated temperature, for example from 50° to 100° C., in particular 70° to 90° C., under reflux and in an inert atmosphere, i.e. using an inert gas, for example nitrogen, which can also contain 2.5 to 10% by volume, preferably 5 to 6% by volume, of oxygen.

After the polymerisation stage, the resulting solution of the terpolymer is added to water, whereupon the terpolymer is precipitated in the form of granules of greater or lesser fineness. This advantageously takes place at a temperature of 0° to 40° C., preferably 10° to 30° C. The polymerisation product is isolated in a generally known manner, for example by filtering off the precipitated terpolymer, washing it and drying it. The terpolymers thus obtained have a molecular weight of 15,000 to 60,000, preferably 25,000 to 35,000.

These terpolymers can be used as hair-setting agents in hair sprays. Care should therefore be taken to ensure that at least half (in general 55 to 100%, preferably 75 to 85%) of the free carboxyl groups present in the terpolymers are neutralised in the finished hair sprays, so that the film-forming polymer resins can be removed from the hair simply by rinsing or by washing.

Advantageously, the carboxyl groups are neutralised by a procedure in which the terpolymers, in the form of a solution in an organic solvent (for example $C_2$–$C_3$-alkanols) which is used as a rule in cosmetics, are reacted with a lower organic base, with or without the addition of water.

Preferred organic solvents are ethanol and propanols. These can be used by themselves or in combination with 0.1 to 20% by weight of water or 1 to 70% by weight of other solvents, for example methylene chloride or trichloroethane. Further co-solvents which can be used according to the invention are alkylene glycol mono-lower alkyl ethers, for example ethylene glycol monomethyl ether, ethylene glycol monoethyl ether or 1-methoxypropanol, and also butan-2-ol or 2,2-dimethyl-4-hydroxymethyl-1,3-dioxalane. Preferred combinations of solvents consist of ethanol and methylene chloride or isopropanol and methylene chloride, it also being possible, if desired, for the said co-solvents to be used concomitantly.

The organic bases have as a rule a total of at most 9 carbon atoms, the longest chain having at most 3 carbon atoms. Examples of suitable lower organic bases are primary or tertiary amines, preferably primary or tertiary alkanolamines, having a total of 2 to 9, preferably 2 to 4, carbon atoms, for example triethanolamine, in particular triisopropanolamine and especially 2-amino-2-methylpropanol or 2-amino-2-methyl-propane-1,3-diol.

To finish the hair-setting preparation, according to the invention, which is used in the form of an aerosol spray, the procedure is as a rule to introduce an aerosol propellent as a gas into the solution resulting from the treatment of the terpolymer with the organic base. As defined, propellents are used in which at least 30% by weight, preferably at least 50% by weight, of the total amount of propellent consists of a halogen-free propellent gas, in particular a hydrocarbon propellent. A further halogen-free propellent gas which can advantageously be used is dimethyl ether.

Suitable hydrocarbon propellents which can be used in the preparation according to the invention are preferably alkanes, for example propane, n-butane and isobutane, and mixtures of these propellents, in particular a mixture of propane and butanes. The hydrocarbon propellents can be combined with other propellent gases, for example with other halogen-free propellent gases such as dimethyl ether, or with halogen-containing propellents such as 1,2-dichloro-1,1,2,2-tetrafluoroethane, dichlorodifluoromethane or, preferably, trichlorofluoromethane.

Preferred propellents which can be used according to the invention are halogen-free hydrocarbons having 1 to 5 carbon atoms, and in particular a mixture of propane and butanes, preferably in a ratio of 1:10 to 1:1.8. Propane and butane can advantageously be used in combination with dimethyl ether or trichlorofluoromethane.

As a rule, the finished hair spray preparations according to the invention contain, based on the total preparation:

0.25 to 6% by weight, in particular 0.5 to 3% by weight, of the neutralised terpolymer,
6 to 85% by weight of the solvent and
10 to 80% by weight of the propellent.

The proportion of ethanol or isopropanol can be less than 20% by weight of the formulation or, in the case of ethanol, even as little as 3% by weight.

To impart certain properties, additives can be incorporated into the air-setting preparations, if desired. Examples of these additives are plasticisers such as phthalic acid esters, glycols and glycerol, lubricants and penetrating agents such as lanolines, protein hydrolysates and other protein derivatives, and also silicones, U.V. absorbers, ethylene oxide adducts and polyoxyethylene-cholesterol, as well as perfumes and dyes. In total, these additives should amount to at most 20% by weight of the terpolymer present in the preparation.

The hair-setting preparations have all the characteristic properties which are required for such products. The films are transparent, shiny, flexible and firm. They possess good antistatic properties, adhere well to the hair and are easily removed by means of surfactant solutions such as shampoos. They make it possible for the hair to be combed easily. Moreover, they do not turn yellow on ageing, nor do they become sticky when exposed to high humidities. In particular, they give an excellent hold under conditions of high humidity.

In the following preparation instructions and examples, percentages are by weight, unless stated otherwise.

Preparation instructions

Instructions A

A solution (1), which contains 75 parts of acrylic acid, 420 parts of ethyl acrylate and 525 parts of N-tert.-butylacrylamide in a mixture of 900 parts of ethanol and 400 parts of water, is prepared and stored under a nitrogen atmosphere containing 6% of oxygen. 10% of solution (1) is then introduced into a reaction vessel containing 100 parts of ethanol and 40 parts of water, which have been heated to the reflux temperature. The remaining 90% of solution (1), and a solution (2), which contains 8.9 parts of tert.-butyl peroctoate in 77 parts of ethanol, are added simultaneously over a period of 1½ to 2½ hours. The heating of the reaction vessel is stopped and the addition of monomer and peroctoate is regulated so that the reflux temperature is maintained by the heat of reaction liberated. This is carried out in such a way that the addition of solution (1) ends 15 to 30 minutes before the addition of solution (2). After the addition of solution (2) has ended, the temperature is kept at 80° C. for a further 3 hours and the mixture is left to react to completion at this temperature. The reaction mass is then cooled to 20°-25° C. and introduced into 7,200 parts of water, with stirring. This gives a granular, non-adhering precipitate, which is filtered off, washed with 5,000 parts of water and dried in vacuo at 40° to 65° C., preferably 40° to 50° C.

Instructions B to F

Further polymers according to instructions B to F are obtained by following the procedure described in instructions A and using the monomers and solvents listed in the following Table 1 in the amounts given (parts by weight).

TABLE 1

|  | Preparation instructions | | | | |
|---|---|---|---|---|---|
|  | B | C | D | E | F |
| N-tert.-butylacrylamide | 578 | 350 | 350 | 535 | 350 |
| Methyl acrylate | — | 242 | — | — | — |
| Ethyl acrylate | 463 | — | — | — | 280 |
| Butyl acrylate | — | — | 358 | 428 | — |
| Acrylic acid | 57.6 | 50 | 50 | 108 | 50 |
| Ethanol | 950 | 820 | 950 | 700 | 900 |
| Isopropanol | — | — | — | 200 | — |
| Acetone | — | — | — | — | 300 |
| Water | 400 | 400 | 250 | 280 | — |

Instructions G 35.5 g of N-tert.-butylacrylamide and 0.24 g of α,α'-azo-bis-isobutyronitrile are initially introduced into a reaction vessel and the apparatus is then flushed with nitrogen for 15 minutes. A solution of 35.8 g of butyl acrylate and 5.1 g of acrylic acid in 88 g of ethanol and 25 g of water is then introduced into the reaction vessel. The reaction mixture is warmed to 80° C.; in this process, the mixture of comonomers dissolves completely and the polymerisation starts. The reaction mixture is stirred for 5 hours at 80° C. and then cooled to 20°-25° C. and the product is precipitated by introducing the reaction solution into 750 g of deionised water, with vigorous stirring of the precipitation bath. This gives a colourless coarse powder, which is filtered off and dried at 60° C. [in vacuo].

Instructions H 30.6 g of N-n-butylacrylamide and 0.25 g of α,α'-azo-bis-isobutyronitrile are initially introduced into a reaction vessel and the apparatus is then flushed with nitrogen for 15 minutes. A solution of 30.7 g of n-butyl acrylate and 10.8 g of acrylic acid in 125 g of ethanol is then introduced into the reaction vessel. On warming to 80° C., the mixture of comonomers dissolves completely and the polymerisation starts. The reaction mixture is stirred for 5 hours at 80° C., then cooled to 20°-25° C. and introduced into 2.5 liters of deionised water, whereby the terpolymer precipitates as a colourless coarse powder. This is filtered off, washed with 1.5 liters of water and dried at 45°-50° C. in vacuo.

Instructions I to P

Further polymers according to instructions I to P are obtained by following the procedure in instructions H and using the monomers listed in the following Table 2 in the amounts given (parts by weight).

TABLE 2

|  | Preparation instructions | | | | | |
|---|---|---|---|---|---|---|
|  | I | K | L | M | N | O | P |
| N-tert.-butyl-acrylamide | — | 31.8 | — | 30.6 | 35.1 | 35.5 | — |
| N-n-butylmeth-acrylamide | — | — | — | — | — | — | 43.8 |
| N-iso-propyl-acrylamide | 36.3 | — | — | — | — | — | — |
| N-methylmeth-acrylamide | — | — | 25.0 | — | — | — | — |
| Ethyl acrylate | 28.4 | — | — | 30.7 | 27.7 | — | 28.4 |
| n-Butyl acrylate | — | 32.5 | — | — | — | — | — |
| Isobutyl acrylate | — | — | 40.4 | — | — | — | — |
| Isobutyl meth-acrylate | — | — | — | — | — | 40.4 | — |
| Acrylic acid | 5.1 | — | — | 8.6 | 7.0 | — | — |
| Methacrylic acid | — | — | 6.1 | — | — | 6.1 | 6.1 |
| Itaconic acid | — | 3.9 | — | — | — | — | — |

EXAMPLE 1

A solution of 1.5 parts of the terpolymer prepared according to instructions A (polymer A) in 38.38 parts of anhydrous ethanol is treated with 0.12 part of 2-amino-2-methylpropanol, about 80% of the carboxyl groups present in the terpolymer being neutralised. The solution is then introduced into an aerosol container into which 60 parts of propane/butane (15:85) are then introduced under pressure. This gives a clear aerosol formulation.

EXAMPLES 2 TO 16

Further clear hair-setting preparations according to Examples 2 to 16 are obtained by following the procedure described in Example 1 and by using the polymers, bases, solvents and propellent gases listed in the following Tables 3 and 4 in the amounts given (parts by weight).

TABLE 3

|  | Example No. | | | | | | | |
|---|---|---|---|---|---|---|---|---|
|  | 2 | 3 | 4 | 5 | 6 | 7 | 8 | 9 |
| Polymer A | 1.5 | — | — | 2.0 | 2.0 | 1.5 | 2.0 | 2.0 |
| Polymer C | — | 2.0 | — | — | — | — | — | — |
| Polymer E | — | — | 1.30 | — | — | — | — | — |
| 96% by volume ethanol | — | 30.0 | — | — | — | — | — | — |
| Absolute ethanol | — | — | 33.57 | — | — | 23.38 | — | — |
| Isopropanol | 13.38 | — | — | 5.0 | 10.0 | — | 12.8 | 17.9 |
| Methylene chloride | 20.0 | — | — | 35.0 | 35.0 | — | 35.0 | 30.0 |
| Water | — | 7.78 | — | — | — | — | — | — |
| Aminomethylpropanol | — | — | 0.13 | 0.15 | 0.15 | 0.12 | 0.2 | 0.1 |
| Aminomethylpropanediol | 0.12 | 0.22 | — | — | — | — | — | — |
| Propane/butane (15:85) | 30.0 | — | 25.0 | 37.85 | 32.85 | 30.0 | 50.0 | 50.0 |
| Trichlorofluoromethane | 35.0 | — | 40.0 | 20.0 | 20.0 | 45.0 | — | — |
| Dimethyl ether | — | 60.0 | — | — | — | — | — | — |

TABLE 4

| | Example | | | | | | |
|---|---|---|---|---|---|---|---|
| | 10 | 11 | 12 | 13 | 14 | 15 | 16 |
| Polymer A | 2.0 | 1.5 | 2.0 | 2.0 | 2.0 | 2.0 | 2.0 |
| Aminomethylpropanol | 0.2 | 0.12 | 0.15 | 0.15 | 0.15 | 0.15 | 0.15 |
| Absolute ethanol | — | — | 3.0 | 3.0 | 3.0 | 3.0 | 3.0 |
| Isopropanol | 32.8 | 13.38 | — | — | — | — | — |
| Methylene chloride | 15.0 | 35.0 | 35.0 | 35.0 | 35.0 | 35.0 | 35.0 |
| Trichlorofluoromethane | — | 20.0 | 20.0 | 20.0 | 20.0 | 20.0 | 20.0 |
| Propane/butane (15:85) | 50.0 | — | 37.85 | 37.85 | 37.85 | 37.85 | 37.85 |
| Dimethyl ether | — | 30.0 | — | — | — | — | — |
| Butan-2-ol | — | — | — | — | — | 2.0 | — |
| Ethylene glycol mono-methyl ether | — | — | 2.0 | — | — | — | — |
| Ethylene glycol mono-ethyl ether | — | — | — | 2.0 | — | — | — |
| *Solketal | — | — | — | — | — | — | 2.0 |
| 1-Methoxypropan-2-ol | — | — | — | — | 2.0 | — | — |

*2-dimethyl-4-hydroxymethyl-1,3-dioxalane

Comparatibility of the polymers with propellent gases

One isopropanol formulation and one ethanol formulation, each of which contains 1.5% of polymer A and 0.12% of 2-amino-2-methylpropanol, are mixed, in an aerosol container, with the propellent gases trichlorofluoromethane, propane/butane or dimethyl ether, or a combination thereof, according to the percentage data in the following Table 5, with or without the addition of methylene chloride or water.

TABLE 5

| | Experiment No. | | | | |
|---|---|---|---|---|---|
| | 1 | 2 | 3 | 4 | 5 |
| Polymer A | 1.5 | 1.5 | 1.5 | 1.5 | 1.5 |
| Alkanol* | 33.5 | 13.5 | 38.5 | 38.5 | 32.5 |
| Methylene chloride | 35.0 | 20.0 | — | — | — |
| Water | — | — | — | — | 6.0 |
| Propane/butane (15:85) | 30.0 | 30.0 | 20.0 | 60.0 | — |
| Trichlorofluoromethane | — | 35.0 | 40.0 | — | — |
| Dimethyl ether | — | — | — | — | 60.0 |

*Alkanol can be ethanol or isopropanol.

Solution stability

One filled container in each case was stored at room temperature and at alternating temperatures (−20°/+50° C.) at 12-hour intervals, for 14 days, and the appearance of the solution at −20° C., +20° C. and +50° C. was then assessed visually.

None of the solutions, which were clear at the start of the test, showed a change on assessment.

Cloud point

The filled containers were slowly cooled to −30° C. None of the test formulations showed turbidity (start of polymer precipitation) at this temperature (standard at −20° to −25° C.).

Permissible excess of propellent

After using a 50% overdose of the corresponding propellent gas, none of the test formulations showed turbidity, which allows a sufficient safety margin.

The hair-setting preparations prepared according to Examples 1 to 16 have an outstanding solution stability under the above experimental conditions, and this stability ensures trouble-free operation of the spray cans, even under extreme climatic conditions. The formulations give the hair a natural, elastic and lasting firmness, even in a humid climate. The feel of the hair remains soft and pleasant, even after repeated application.

What is claimed is:

1. A hair-setting preparation, which comprises:
   (1) a solution of 0.25 to 6% by weight of a terpolymer prepared from a mixture of 45 to 55% by weight of N-t-butylacrylamide, 35 to 45% by weight of ethyl acrylate and 5 to 8% by weight of acrylic acid and 6 to 85% by weight of a solvent selected from the group consisting of ethanol isopropanol and mixtures thereof, with 55% to 100% of the carboxyl groups in the terpolymer having been neutralized by a primary or tertiary alkanolamine having a total of 2 to 9 carbon atoms, the longest chain having at most 3 carbon atoms; and
   (2) from 10 to 80% by weight of a propellant which consists essentially of a halogen-free hydrocarbon, dimethyl ether, or mixtures thereof.

2. The preparation of claim 1, wherein the primary alkanolamine has a total of 2 to 4 carbon atoms.

3. The preparation of claim 1, wherein the alkanolamine is 2-amino-2-methylpropanol, 2-amino-2-methylpropane-1,3-diol or triisopropanolamine.

4. The preparation of claim 1, wherein 75 to 85% of the carboxyl groups in the terpolymer are neutralized.

5. The preparation of claim 1, wherein the propellant is propane, butane or isobutane, or a mixture thereof.

* * * * *